(12) United States Patent
Akiva

(10) Patent No.: US 6,341,229 B1
(45) Date of Patent: Jan. 22, 2002

(54) WEARABLE APRON FOR USE IN EGG AND OTHER MEDICAL TESTS

(75) Inventor: Sharon Akiva, Caesarea (IL)

(73) Assignee: Tapuz Medical Technology Ltd., Caesarea (IL)

( * ) Notice: Subject to any disclaimer, the term of this patent is extended or adjusted under 35 U.S.C. 154(b) by 0 days.

(21) Appl. No.: 09/326,641

(22) Filed: Jun. 7, 1999

(30) Foreign Application Priority Data

Jun. 14, 1998 (IL) .................................................. 124900

(51) Int. Cl.[7] ..................... A61B 5/0402; A61B 5/0205; A61B 5/053; A61B 5/01; A61B 5/08
(52) U.S. Cl. ...................... 600/388; 600/390; 600/393; 600/483; 600/484; 600/528; 600/536; 600/547; 600/549
(58) Field of Search ................................. 600/388–390, 600/393, 483, 484, 528, 536, 547, 549

(56) References Cited

U.S. PATENT DOCUMENTS

| 4,129,125 A | * | 12/1978 | Lester et al. | 600/484 |
|---|---|---|---|---|
| 4,308,870 A | * | 1/1982 | Arkans | 600/484 |
| 4,517,982 A | * | 5/1985 | Shiga et al. | 600/484 |
| 4,580,575 A | * | 4/1986 | Birnbaum et al. | 600/484 |
| 4,784,162 A | * | 11/1988 | Ricks et al. | 600/484 |
| 4,889,131 A | * | 12/1989 | Salem et al. | 600/484 |
| 4,966,154 A | * | 10/1990 | Cooper et al. | 600/484 |
| 5,224,479 A | * | 7/1993 | Sekine | 600/389 |
| 5,238,001 A | * | 8/1993 | Gallant et al. | 600/483 |

FOREIGN PATENT DOCUMENTS

| WO | 8805282 | * | 7/1988 | 600/528 |
|---|---|---|---|---|
| WO | 97/14346 | | 4/1997 | |

* cited by examiner

*Primary Examiner*—Lee Cohen
(74) *Attorney, Agent, or Firm*—Lowe Hauptman Gilman & Berner, LLP

(57) ABSTRACT

Disclosed is a wearable multifunctional examination apron for use in ECG and other medical tests. The apron includes a number of ECG electrodes for performing ECG tests, and a number of microphones for heart and lung auscultation. The ECG test signals and heart/lung sounds are transferred to a processing unit, and processed therein. Test results are then displayed on a built-in display device, and/or transmitted to external devices for evaluation. The ECG electrodes can also be used in chest wall movement tests. The apron further includes a temperature sensor and an inflatable cushion for body temperature and blood pressure measurements.

24 Claims, 5 Drawing Sheets

WEARABLE APRON FOR USE IN EGG AND OTHER MEDICAL TESTS

FIELD OF THE INVENTION

The present invention relates to wearable pads for use in medical tests, and more particularly, to a multifunctional wearable apron for use in examining heart functions, lungs functions, blood pressure and additional tests.

DESCRIPTION OF THE RELATED ART

In order to perform an ECG test on a patient, one must place and attach electrodes on various locations patient body. One of the means to attach electrodes to a patient body in exact placements is an Electrode Apron disclosed in PCT publication No. WO97/14346. The Apron is designed to be put on patient body and includes electrodes placed at desired locations to perform required tests.

SUMMARY OF THE INVENTION

The present invention provides an Examination Apron that independently performs ECG and other examinations. The Examination Apron, according to the present invention, performs ECG test and additional tests and can display the results on a display screen installed on the Examination Apron and transfer data and results via cable or IR (Infra Red) LED to outside instruments such as printers, PCs and modems.

The Examination Apron of the present invention independently performs ECG and other examinations and includes a 12 Lead Electrodes Apron that is put on patient body, a processing microcomputer unit for receiving data from the electrodes and additional equipment installed on the Examination Apron, an optional display device for displaying tests results that were calculated and processed by the processing unit, a cable or IR LED for transmitting information from the processing unit to a receiving instrument such as a personal computer, a modem or a printer. The Examination Apron includes a battery that provides the power needed for operation.

The Examination Apron can, additionally, perform a Chest Wall Movement test by means of the hardware and software in the processing unit. That processing unit sends a high frequency current to the existing ECG electrodes, measures changes in impedance caused by the Chest Wall Movements, thus calculating test results.

The Examination Apron, can, in addition, include microphones to enable auscultation to the heart from various standard points on the chest such as the pulmonary and aortal points, ERB and APEX by means of the microphones placed in the Examination Apron above these listed points. The location of the microphones is adjusted to the patient body size by stretching the Apron on the body.

The Examination Apron further includes back straps provided with additional microphones for auscultation to lungs. These additional microphones will be placed above different fields of each lung—one or more microphones will be placed above the lower lobe and one or more microphones will be placed above the upper lobe.

The Examination Apron can, in addition, include a temperature sensor pressed with the Apron to the body. In that manner the patient body to in the axial region is measured, transferred to the processing unit and then displayed or transmitted to external devices.

The Examination Apron can, in addition, include an inflatable cushion attached to the patient body. By an inflating device, manually operated or electrally driven, the cushion can be inflated or deflated. The pressure values are translated into digital data by a transducer and from this data, the blood pressure of the patient is calculated.

The present invention will be described in details with reference FIGS. 1,2,3 and 4. The figures are intended to describe embodiments of the invention and not to restrain the scope of the invention in any way.

DETAILED DESCRIPTION OF THE INVENTION

Figure 1:
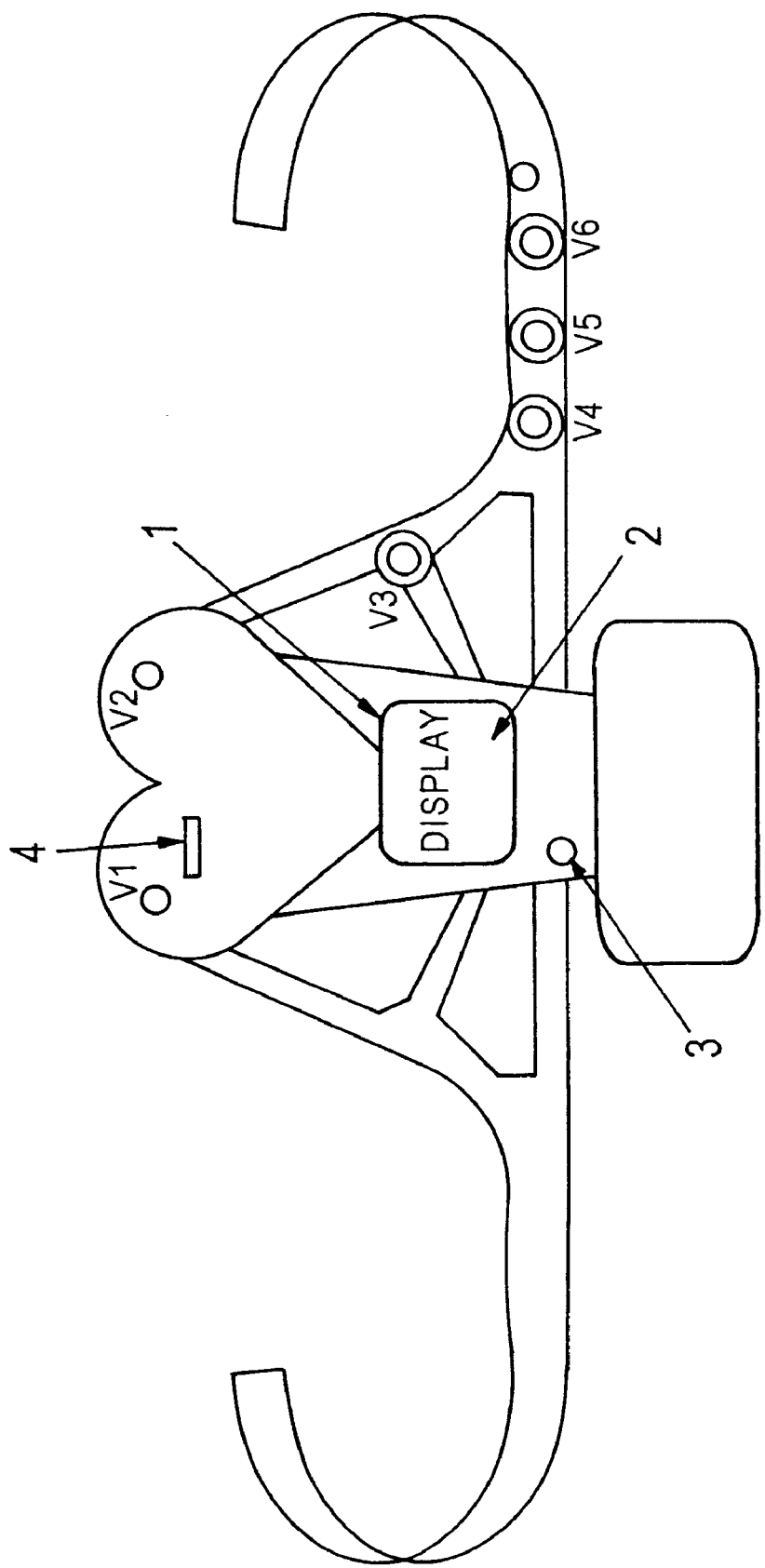
FIG. 1 shows the Examination Apron including an ECG machine.

FIG. 1 shows the Examination Apron of the invention. The electrodes are placed on the Apron on standard locations. Inside the central part of the Apron a processing unit is installed (1). It receives the ECG signals from the electrodes and calculates the ECG leads. The result is displayed on a display device (2) that can be installed in the front part of the Examination Apron. By means of IR LED (3), the processing unit transmits the ECG information to a printer, PC or modem The Apron includes battery (4) that provides the Apron with all the power it requires to operate.

Figure 2:
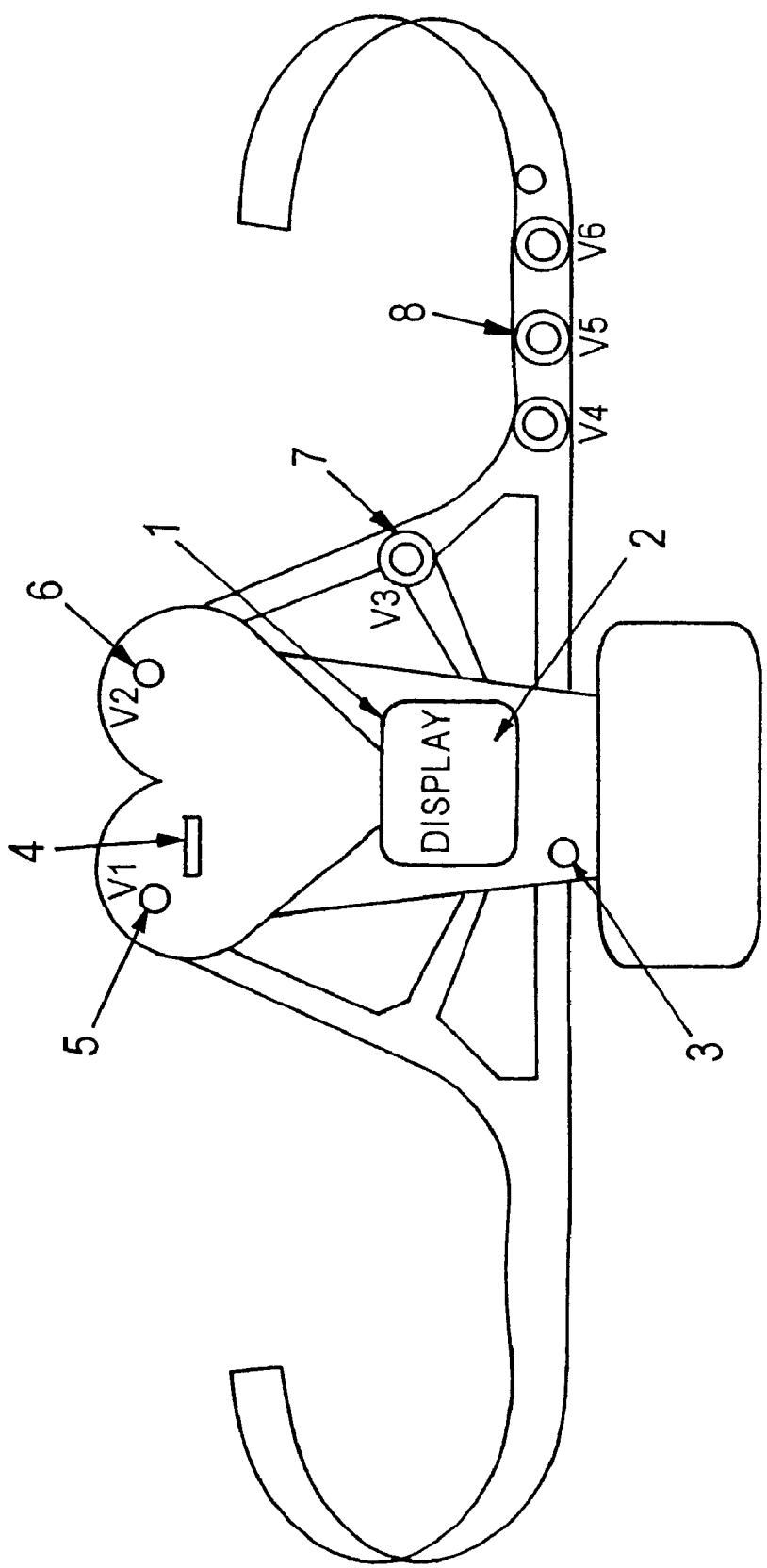
FIG. 2 shows the Examination Apron including an auscultation system.

FIG. 2 shows the Examination Apron provided with an auscultation system. Microphones are installed in several points within the Apron. The microphones record the sounds of the heartbeat from several points on patient chest. For instance, we can install one microphone in electrode V1 (5) is listening to Pulmonary point, one microphone in electrode V2 (6) for listening to Aortal point, the microphone in electrode V3 (7) for listening to ERB point and the microphone in electrode V5 (8) for listening to APEX point. The information is transmitted to the processing unit (1) and the result is displayed on the display device (2) and can be transmitted by IR LED (3) to outside receiving means, so that a physician can listen to the patient heart from a remote location.

Figure 2A:
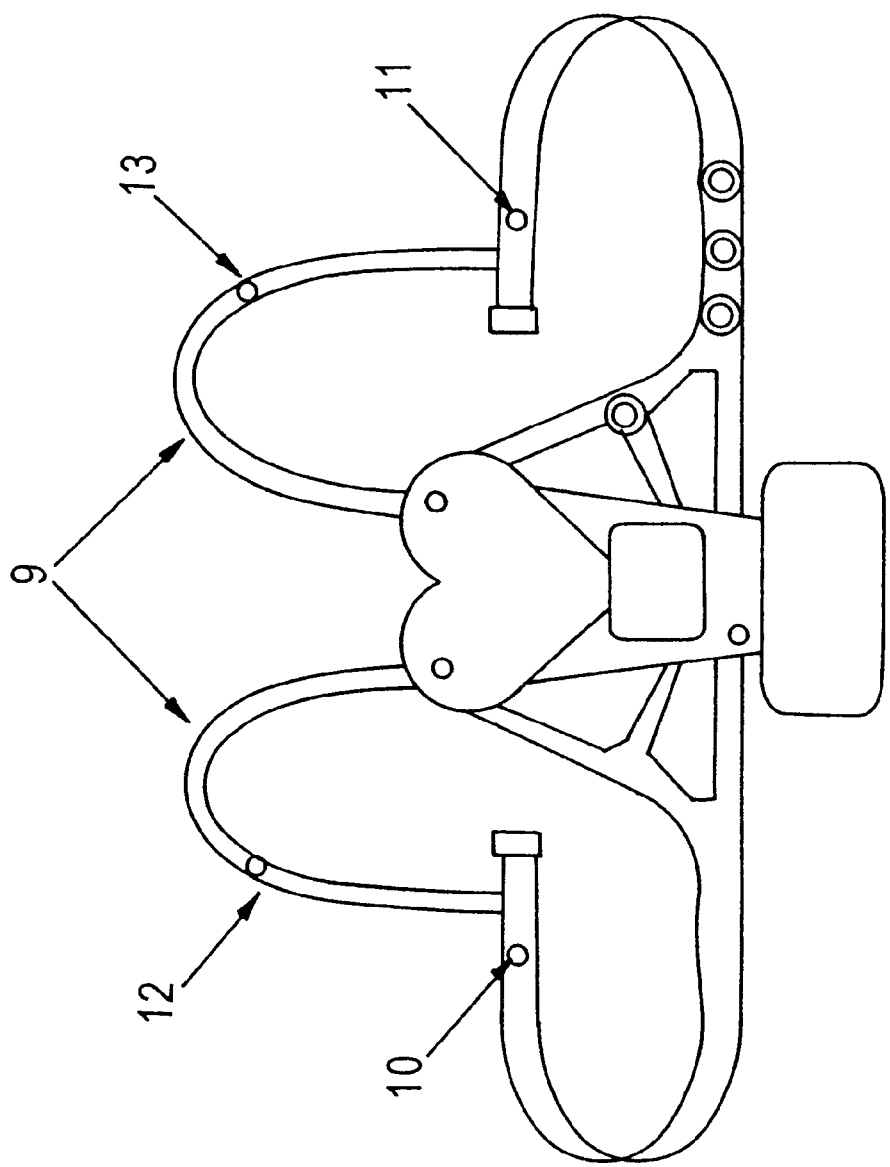

FIG. 2*a* shows another embodiment of the Apron that includes back straps (9) provided with four additional microphones—10 and 11 above the lower lung lobes and 12 and 13 above the upper lung lobe, for recording the breathing sounds of the patient in order to transfer them to a remote medical facility for evaluation.

Figure 3:
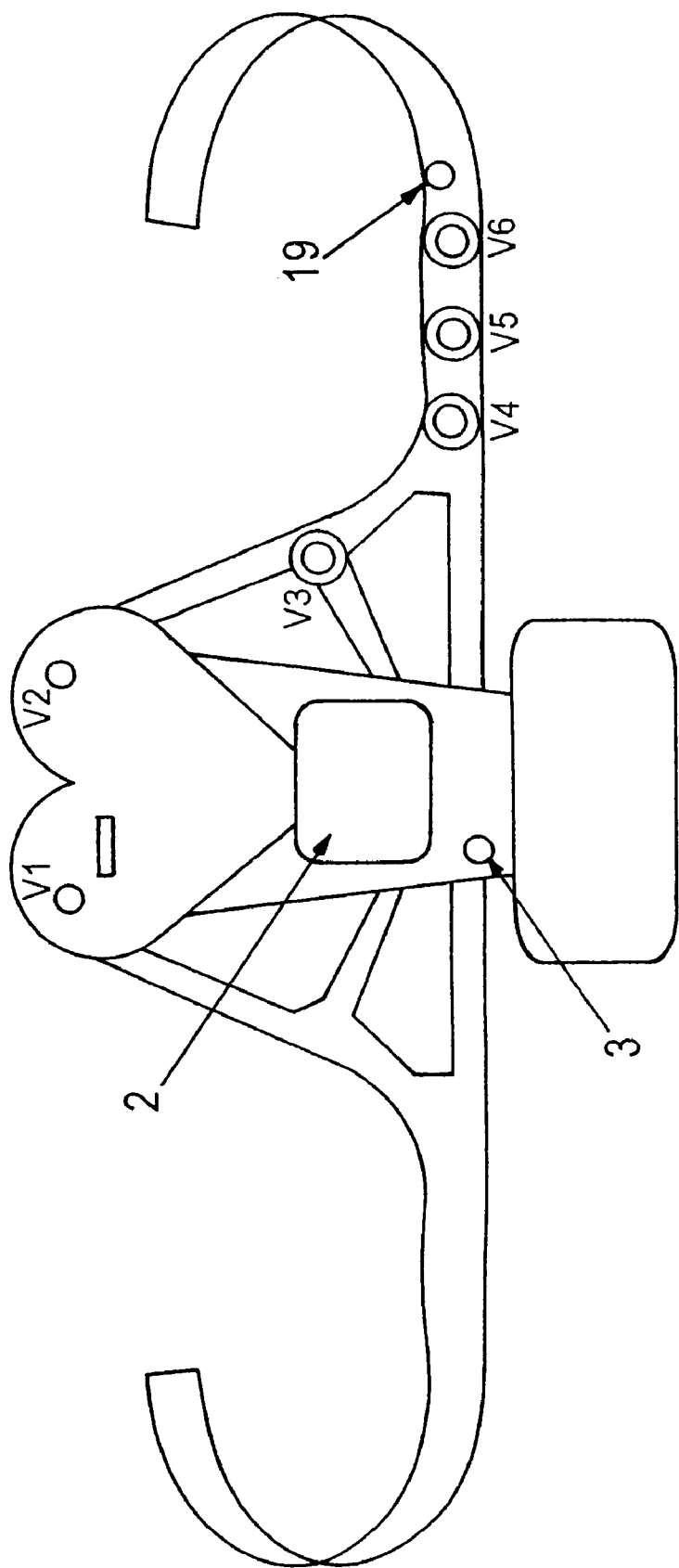
FIG. 3 shows the Examination Apron including a temperature sensor.

FIG. 3 shows the Apron provided with a temperature sensor (19). The temperature sensor is installed on the Apron. When the Apron is being put on the patient, the sensor is pressed to the patient body in the same way the electrodes are pressed to it. The temperature sensor measures the temperature of the patient axial area and displays the result on the display device (2). The result can also be transmitted to outside receiving devices by the IR LED.

Figure 4:
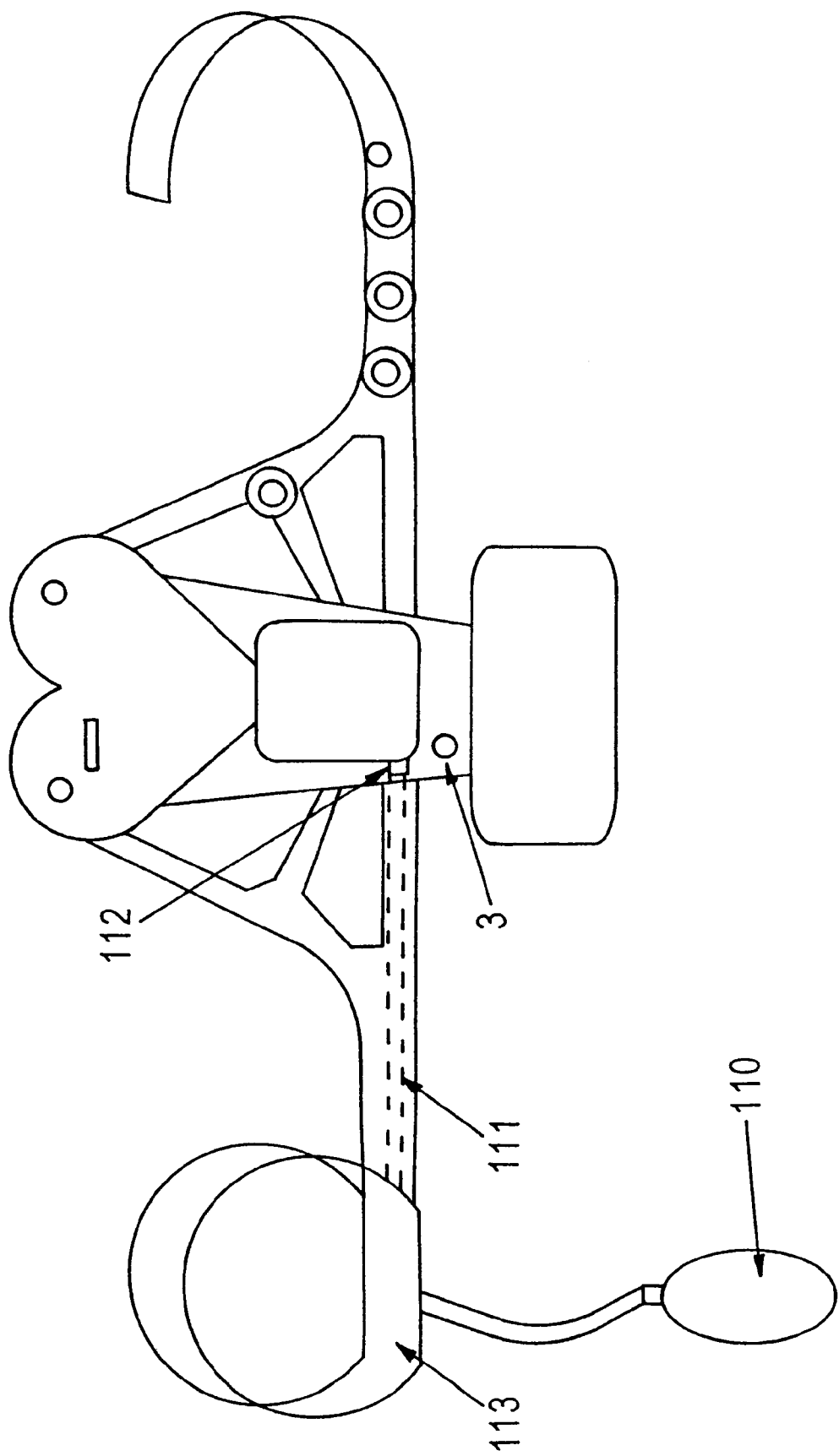
FIG. 4 shows the Examination Apron including a Blood Pressure testing system.

FIG. 4 shows the Apron provided with a Blood Pressure testing system. Into the part of the Apron that is attached to an arm of the patient an inflatable cushion is installed (113). The inflatable cushion can be inflated and deflated by an inflating device (110) that can be either manually operated or electrically driven.

The pressures are transmitted through a tube (111) into a converter (112) that translates the pressures into a digital form. The processing unit calculates the patient blood pressure from that information and displays it on the display device (2). The information can also be transmitted by IR LED (3) to outside receiving devices.

The Examination Apron of the present invention can perform independently several tests, display the results on a display device and transmit the results to an outside receiving devices. The Apron operates on its' own power supply, such as batteries. The examinations performed by the Apron are: ECG test, Chest Wall Movement, Heart and Lung auscultation—in standard medical auscultation points, patient temperature measuring and Blood Pressure tests.

What is claimed is:

1. An examination apron, wearable on an upper body portion of a patient for independently performing medical examinations of the patient, the examination apron comprising:

a plurality of ECG electrodes arranged on the examination apron for detecting ECG signals of the patient;

a plurality of microphones arranged on the examination apron for recording heartbeat sounds of the heart of the patient from predetermined standard points on the chest of the patient, wherein at least one of the ECG electrodes and at least one of the microphones are placed adjacent or integrated on the examination apron;

a processing unit for receiving and processing at least one of the detected ECG signals from the ECG electrodes and the recorded heartbeat sounds from the microphones, and generating at least one of an ECG test result and a heart auscultation test result; and an output device for outputting said at least one of the ECG test result and the heart auscultation test result.

2. The examination apron of claim 1, wherein the microphones are arranged on the examination apron so as to be placed above the standard points when the examination apron is being worn by the patient.

3. The examination apron of claim 1, wherein the standard points include pulmonary, aortal, ERB and APEX points.

4. The examination apron of claim 3, wherein said at least one ECG electrode and said at least one microphone are arranged on the examination apron so as to be placed above one of the listed standard points.

5. The examination apron of claim 4, wherein at least two of the ECG electrodes and at least two of the microphones are arranged on the examination apron so as to be placed above at least two of the listed standard points, respectively.

6. The examination apron of claim 1, wherein the output device includes a display for presenting said at least one of the ECG test result and the heart auscultation test result.

7. The examination apron of claim 1, wherein the output device includes a communication interface for transmitting said at least one of the ECG test result and the heart auscultation test result to external devices.

8. The examination apron of claim 7, wherein the communication interface includes one of an IR LED and a cable.

9. The examination apron of claim 7, wherein said communication interface is configured to communicate with at least one of a PC, a modem, and a printer.

10. The examination apron of claim 1, further including at least a battery as a power source for at least one of the ECG electrodes, microphones, processing unit, and output device.

11. The examination apron of claim 1, wherein the processing unit is further adapted to measure impedance between predetermined ECG electrodes, and to generate a chest wall movement test result based on the measured impedance.

12. The examination apron of claim 11, wherein the processing unit measures the impedance by applying a high frequency current to the predetermined ECG electrodes.

13. The examination apron of claim 11, wherein the chest wall movement test result is outputted by the output device.

14. The examination apron of claim 1, further including a set of additional microphones for recording lung sounds of the patient, the additional microphones are arranged on the examination apron so as to be placed above at least one of a lower lobe and an upper lobe of at least one lung of the patient when the examination apron is being worn by the patient.

15. The examination apron of claim 14, wherein the processing unit generates a lung auscultation test result based on the recorded lung sounds, and the lung auscultation test result is outputted by the output device.

16. The examination apron of claim 1, further including a temperature sensor for measuring a temperature in an axial region of the patient.

17. The examination apron of claim 16, wherein the processing unit generates a temperature test result based on the sensed temperature, and the temperature test result is outputted by the output device.

18. The examination apron of claim 1, further including an inflatable cushion for detecting blood pressure of the patient, the inflatable cushion communicated with a converter for converting the detected pressure into machine-readable data to be fed to the processing unit.

19. The examination apron of claim 18, wherein the processing unit generates a blood pressure test result based on the machine-readable data, and the blood pressure test result is outputted by the output device.

20. The examination apron of claim 1, wherein the processing unit includes a microcomputer.

21. The examination apron of claim 1, including a central chest pad corresponding to the chest of the patient and two side harnesses, wherein the ECG electrodes, microphones, processing unit, and output device are arranged on at least one of the chess pad and side harnesses.

22. The examination apron of claim 21, wherein at least one of the side harnesses includes an inflatable cushion for detecting blood pressure of the patient, the inflatable cushion communicated with a converter for converting the detected pressure into machine-readable data to be fed to the processing unit.

23. The examination apron of claim 22, wherein the inflatable cushion communicated with the converter via a tube incorporated in the examination apron.

24. The examination apron of claim 1, wherein more than one of the ECG electrodes and more than one of the microphones are placed adjacent or integrated on the examination apron.

* * * * *

UNITED STATES PATENT AND TRADEMARK OFFICE
CERTIFICATE OF CORRECTION

PATENT NO. : 6,341,229 B1
DATED : January 22, 2002
INVENTOR(S) : Sharon Akiva

It is certified that error appears in the above-identified patent and that said Letters Patent is hereby corrected as shown below:

<u>Title page,</u>
Item [54], Title should read -- WEARABLE APRON FOR USE IN ECG AND OTHER MEDICAL TESTS --

Signed and Sealed this

Twenty-seventh Day of August, 2002

*Attest:*

*Attesting Officer*

JAMES E. ROGAN
*Director of the United States Patent and Trademark Office*